United States Patent [19]

Kaufman

[11] Patent Number: 4,755,048
[45] Date of Patent: Jul. 5, 1988

[54] OPTICAL ANALYSIS OF IMPURITY ABSORPTIONS

[75] Inventor: R. Gilbert Kaufman, Chicago, Ill.

[73] Assignee: Amoco Corporation, Chicago, Ill.

[21] Appl. No.: 922,165

[22] Filed: Oct. 23, 1986

[51] Int. Cl.[4] .......................... G01N 21/25; G01J 3/42
[52] U.S. Cl. .................................... 356/407; 356/319; 356/320; 250/574
[58] Field of Search ............... 356/319, 320, 323, 338, 356/342, 343, 407; 250/574

[56] References Cited

U.S. PATENT DOCUMENTS 4,101,222 7/1978 Mathisen .................... 356/319 X
4,459,024 7/1984 Gergely ....................... 356/342 X
4,669,878 6/1987 Meier ............................... 356/319

FOREIGN PATENT DOCUMENTS 0155741 9/1984 Japan ................................ 356/338

Primary Examiner—Eugene R. LaRoche
Assistant Examiner—David Mis
Attorney, Agent, or Firm—Richard A. Kretchmer; William H. Magidson; Ralph C. Medhurst

[57] ABSTRACT

Optical apparatus and methods are employed in the determination of impurity components present in both homogenous and non-homogenous light-scattering products. Light sources having wavelengths in the visible and near-infrared regions are preferred.

35 Claims, 3 Drawing Sheets

REFLECTION SPECTRA
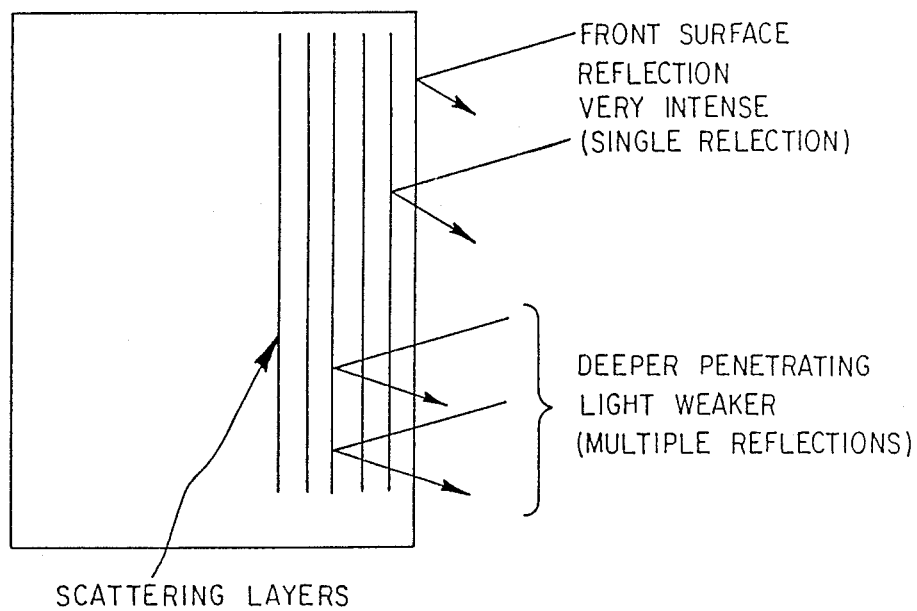
FIG. 1
FIG. 2
SCATTERED LIGHT SPECTRA
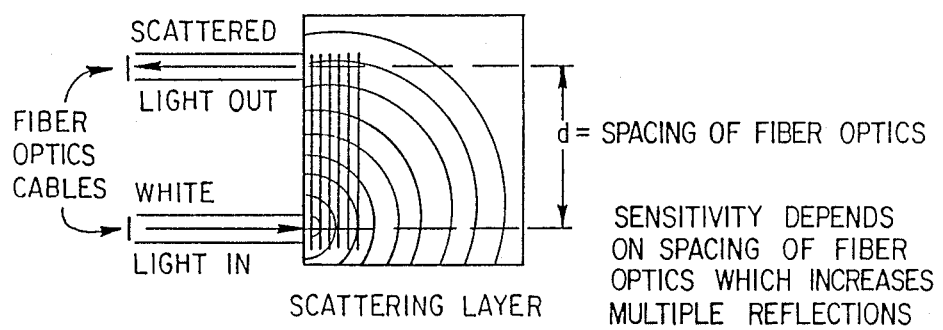

OPTICAL ANALYSIS OF IMPURITY ABSORPTIONS

This invention relates to sensor apparatus and its use in employing reflected scattered light to measure impurity absorptions in light-scattering media which may be either homogeneous or non-homogenous. Particularly preferred apparatus employs fiber optics.

BACKGROUND OF THE INVENTION

Many commercial solid products include a color measurement in their specifications. Indeed, with many light-colored solid products, generally employed as intermediates, the color specification is of critical importance. This is true of both organic and inorganic materials. As one example, the shipping specification for purified terephthalic acid (PTA) is a color measurement.

In light-colored, or white, solids, such as PTA, the degree of yellowness is generally taken as a measurement of the degree of impurity. There is employed, as a measure of yellowness, a function characterized as the b-value, generally described in Hunter, Richard S., *The Measurement of Appearance*, John Wiley & Son (New York), 1975, pages 122–123. The b-value typically has a maximum value at a wavelength of about 450 nanometers (nm) and a half width of about 60 nm. In the case of PTA, variations in the b-value are typically less than the human eye can detect, thus requiring very sophisticated reflectance spectrophotometric equipment for its measurement. This is a time-consuming procedure, poorly adapted to use with a continuous non-homogeneous production line for a critical product. Typically, thousands of pounds of product are prepared during the interval between analyses.

The sensor apparatus of this invention is capable of being inserted directly into a product outlet (e.g., dryer) line to provide a continuous on-line determination of the b-value, coupled with an ability to measure other selected wavelengths of scattered light.

Reflectance measurements are limited in that there is no simple method for increasing sensitivity other than developing equipment capable of measuring reflected light intensity to more significant figures. The illustration presented in FIG. 1 shows the development of reflectance spectra in light-scattering systems. Deeper penetration of light, providing multiple reflections, generates weaker signals which are, at the same time, preferred because they are more precise in the information they can afford. Again, the sensor apparatus of this invention can readily be adapted for increased sensitivity by increasing the distance between the source of light scattering and the point of analysis.

An extensive discussion of reflectance analysis employing scattered light in the near-infrared has been published in *Analytical Chemistry*, vol. 55, p. 1165A (1983).

Means generally available for the requisite light transmission for utilizing reflectance spectra have been both inconvenient as to size and inefficient as to loss of signal intensity. While not required for the practice of this invention, the use of fiber optics greatly improves the sensor efficiency and the convenience of its application.

Fiber optic cables have received great attention and development in the broad field of communications. Other adaptations having significant utility have also been developed.

For example, the use of fiber optics in apparatus for measuring airborne solids during environmental surveillance is described in U.S. Pat. No. 4,459,024. Fiberoptic cables are employed in pairs to provide light output and to receive scattered light from particles of airborne pollution. Finally, an information processor is employed to evaluate the scattered light signals.

Recently, a fiber optic probe and transmission system has been employed with a scanning spectrophotometer, as described in *Chemical Engineering*, Dec. 9/23 (1985), p. 37. This system employs light having wavelengths varying from the ultraviolet (250 nm) to the near-infrared (2,200 nm).

Although the methods and instrumentation presently known in the art find widely differing usages, there is a need for an analytical unit having utility in accurately determining trace impurity levels in a broad range of light-scattering media, particularly those which are non-homogeneous with respect both to space and time.

DESCRIPTION OF THE DRAWING

The drawings employed in the description of the invention of this disclosure are illustrative thereof but impose no limitations thereon.

FIG. 1 illustrates the basic nature of reflectance spectra.

FIG. 2 illustrates the phenomenon of introducing white light, effecting scattering, and transmitting scattered light from the sampling system.

SUMMARY OF THE INVENTION

Figure 3:
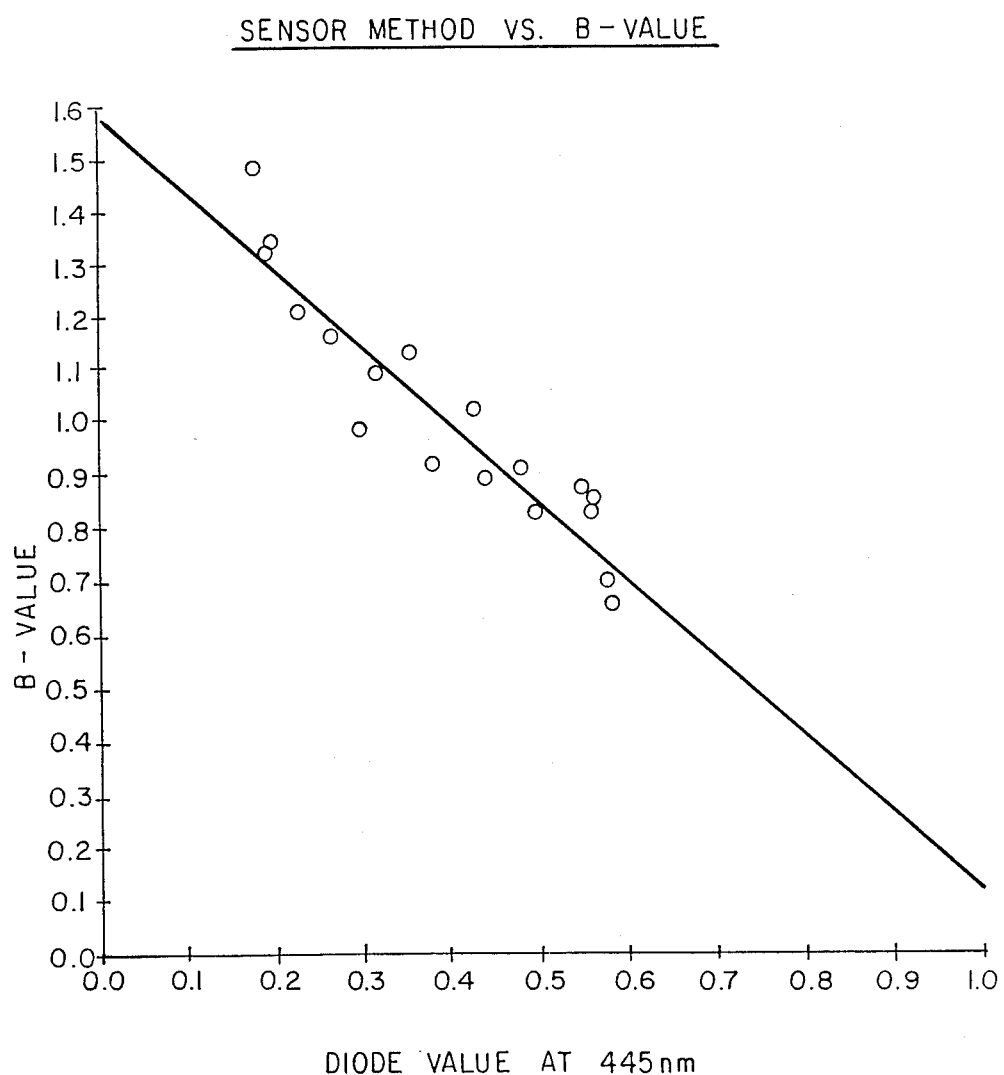
FIG. 3 presents a correlation of b-value for samples of PTA with their respective diode values at a selected wavelength, employing the apparatus and method disclosed herein.

This invention relates to the use of optical sensor apparatus and methodology employing the reflectance of scattered light to measure trace impurity absorptions in various light-scattering media.

It is an object of this invention to provide quantitative analytical sensor apparatus, preferably employing an optical fiber element to supply light to a product contained in a sampling device and additional optical fiber elements to transmit scattered light frequencies to a programmed signal processor. The various optical fiber elements are preferably maintained in a fixed spatial arrangement afforded by a sensor head which provides an optimized spacing of light supply and transmission fiber elements.

It is also an object of this disclosure to provide sensor apparatus capable of use with a broad range of light-scattering media, ranging from concentrated, generally nonhomogeneous particulate solids in air to dilute, generally homogeneous particulate solids in liquid slurries, and to certain liquid-liquid systems.

It is another object of this invention to provide sensor apparatus capable of use with flowing process streams as well as substantially static samples of a light-scattering medium.

It is a further object of this invention to provide an improved method for the quantitative determination of trace impurity components in a light-scattering product.

In a particular embodiment of this invention the sensor apparatus and analytical method of this disclosure are adapted for unusually effective application to the determination of impurity and color levels in purified terephthalic acid contained in a flowing process stream.

In another particular embodiment of this invention the sensor apparatus and analytical method of this disclosure are surprisingly adapted for the determination of impurity and color levels in dilute aqueous clay slurries.

Other objects of the invention of this disclosure will be evident from the following detailed descriptions.

DETAILED DESCRIPTION OF THE INVENTION

The invention of this disclosure relates to novel sensor apparatus and to methods for its use in the quantitative estimation of the impurity level in products having the ability to scatter light, particularly from light sources having wavelengths in the visible and near-infrared regions of the spectra.

The sensor apparatus of this invention requires (a) a source of light which affords useful wavelengths, (b) a vessel or other suitable means to hold the product sample, (c) a spectrophotometric analyzer comprising an array of photodetectors, fitted with appropriate filter elements, and (d) a signal processor system for quantifying the observed intensities of selected wavelengths characteristic of the scattered light. The sensor apparatus further requires communications means for transmitting light to the product sample, collecting selected wavelengths of reflected scattered light, and transmitting the selected wavelengths to the signal processor system. The invention of this disclosure preferably utilizes optical fiber elements, as shown in FIG. 2, either singly or in a plurality contained within a cable, as the means for communication of light to the sequence of critical members comprising the sensor apparatus. Selected optical fibers, generally comprising glass or fused quartz, possess the ability to repeatedly reflect light internally at their walls with negligible loss along the length of the fibers.

The impurity absorptions measured with the sensor apparatus of this invention are generally not amenable to conventional spectrophotometric techniques and, indeed, may represent a very poor optical quality. It has been found that bringing scattered light out of the product sample for optical analysis, as shown in FIG. 2, is a more effective and surprisingly more sensitive technique for observing impurity absorption than the usual head-on reflection spectra which produce high intensity front surface reflection. Similarly, improved results are noted for the fiber optics means for introducing the illuminating light into the light-scattering sample. Accordingly, the practice of this invention permits the effective measurement of spectra of a great variety of materials, both solid and liquid, including comminuted or powdered metal oxides, inorganic salts, clays, minerals, solid organic derivatives, sugars, polymer chips, and proteins, as well as solid-liquid slurries and liquid-liquid systems having a light-scattering component. These latter systems include suspensions, sols, and gels. The material for analysis may typically be a static sample or contained in a flowing process stream.

In the practice of this invention the sampling means, including a receptacle for the sample where necessary, may include a section of product line where the product is analyzed while contained in the flowing product stream. Alternatively, a grab sample may be taken from the process stream for analysis separate from the process equipment. In other instances, any suitable container may be employed in the analysis of slurries and other liquid-containing materials.

The light source employed in this invention will depend upon the selection of the wavelength or wavelengths of scattered light taken as characteristic of the product sample and the impurities to be quantified. Generally, the reference light source is a polychromatic light having useful wavelengths within the range from about 400 nm to about 1,200 nm, preferably from about 400 nm to about 1,000 nm, thus embracing the visible and near-infrared spectral regions.

The spectrophotometric analyzer of this invention may be any such instrument having a plurality of photodetectors, preferably silicon photodiodes, each receiving a selected wavelength of the scattered light and transmitting the characterization thereof to the signal processor means. In turn, the signal processor responds to the characterization of the respective wavelengths, as, for example, by intensity of the signal, to quantify the concentration level of the impurity components in accordance with a pre-determined algorithm that generalizes an impurity level as determined by optical absorption.

The preferred optical fiber elements, singly or in cables containing a plurality of such elements, provide an important feature of this invention. Where employed with a fixed sampling means, the ends of the elements associated with the sampler system may be permanently affixed thereto in a pre-determined spaced relationship. More generally, whether in use with flowing streams or with static sample containers, it is desirable to employ the various optical fiber elements in a fixed spatial arrangement that is also movable to accommodate an optimized sampling and testing procedure. In this latter instance, the ends of the optical fiber elements intended to be inserted into the illuminated product sample are fixedly attached to a flat plate, the end sections of the fibers preferably being parallel to each other and perpendicular to the plane of the flat plate. Such a sensor head may be inserted directly into a product sample, whether static or in a flowing system. In the latter instance, the product stream should flow in a plane perpendicular to the plane of the fixed fiber elements.

The optimum spatial arrangement of the respective optical fiber elements in the sensor head has been found to vary with the particle size of particulate solid product samples. With fine particles, all of the fibers may be contained in a cable with the light source fiber element being centrally located. In more typical powders the light source and scattered light transmission elements are preferably farther apart. With still larger particles such as polymer chips the different elements may be so far apart as to permit the use of a sensor head wherein the types of fiber elements are affixed at right angles to each other. A summary of the correlation of particle size to the distance factor separating the types of optical fiber elements is presented in Table I.

There must be a sufficient number of elements transmitting scattered light to the analyzer to provide characterizations of the impurity components and the product, the latter providing a characterization of the scattered light to correct for differences in concentration and distribution of the product as a function of time. There must also be provided an element measuring light intensity at a wavelength where there is minimal absorption from either impurity components or product. Accordingly, a minimum of three wavelengths is needed to measure a non-homogeneous dispersed system. Thus, a simple unit for the practice of this invention will employ only three wavelengths with appropriate optical interference filters, and individual silicon diodes or detectors.

Some products, such as PTA, may have their own absorption band which is readily distinguished from impurity absorption bands.

In other instances the product characterization may require the addition of a minor quantity of an external substance as an optical marker. Such optical markers are conveniently employed, particularly with flowing process streams, in situations where the marker may subsequently be removed or may lead to no disability. Preferred marker substances include various organic dyes, metal salts, and mixtures of these.

In the case of the organic dyes, these may be employed in either the absorption or the fluorescent mode, the latter mode being more sensitive by a factor of from 3 to 6 magnitudes.

In analyses conducted in accordance with the invention of this disclosure it is generally preferred to select as characteristic of the impurity components a wavelength within the range from about 400 to about 550 nm, most preferably from about 445 to about 450 nm. Similarly, as characteristic of the product, a preferred wavelength for the optical marker band is generally within the range from about 680 nm to about 730 nm.

The sensor apparatus of this invention does not directly measure the b-value (yellowness factor) of product samples but rather the intensity of scattered light at selected wavelengths, so that the b-value may be inferred from correlation to reflectance measurements. Such a correlation is presented in FIG. 3 for purified terephthalic acid (PTA) employing the reflection absorption at a wavelength of 445 nm.

Figure 4:
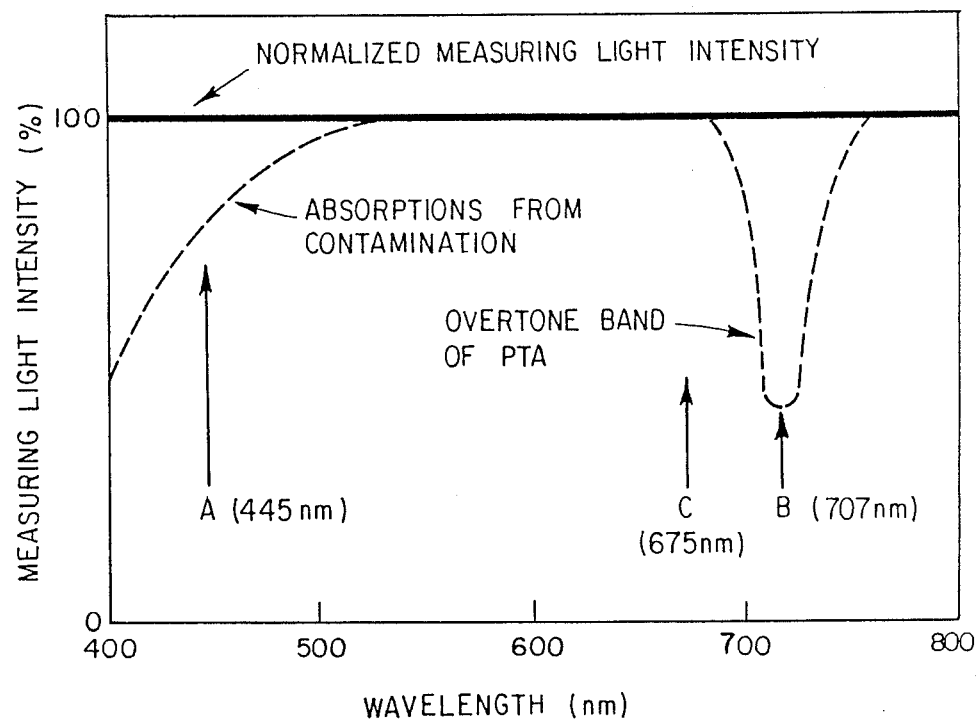
FIG. 4 is illustrative of the absorption spectra characteristic of impurities and of product.

In applying the method of this invention to analysis and quality control of PTA, it was surprisingly found, as shown in FIG. 4, that an excellent absorption for characterizing the product occurred at a wavelength within the range from about 700 to about 710 nm, preferably about 703–707 nm, identified with a stretch overtone band of PTA. This constitutes an elegant intrinsic, or internal, optical marker for PTA. This observation suggests a broad utility for the method in analysis of hydrocarbon-based materials since such materials inherently possess carbon-hydrogen stretch overtone bands.

As illustrated in FIG. 4, in addition to absorption band A for impurity components, absorption band C, the overtone band of the product, and the preferred absorption band B for the product, there are broad absorption areas between bands A and C as well as at still longer wavelengths than C. The background measurements may come from any of these other spectral areas that contain no absorption characteristics of either the impurity components or the product.

Another application of the method of this invention to poor optical systems involves slurries of solid particles in a liquid medium, such as water. It has been found that excellent correlations can be obtained employing slurries having from about 10 to about 50 wt. % of a processed clay, such as kaolin. A preferred concentration range is from about 25 to about 35 wt. %, most preferably about 30 wt. % clay.

In this application, scattered light at a wavelength within the range from about 400 to about 550 nm, preferably about 450 nm, can be employed to characterize the impurity level in the kaolin. The kaolin can be characterized employing wavelengths within the range from about 660 to about 730 nm, and particularly wavelengths of 670 nm and 720 nm. It has surprisingly been found that no background absorption is required where the concentration is accurately known and the slurry is sufficiently dilute to be readily maintained in a homogeneous suspension.

The following examples are illustrative, without limitation, of the invention of this disclosure.

EXAMPLE I

Sensor apparatus was assembled including a tungsten-halogen lamp, a ⅛" fiber optic cable leading from the lamp to a flat optical head, and a ¼" fiber optic cable leading away from the flat optical head. The optical head comprised a flat aluminum plate having holes drilled to receive the respective fiber optic cables in a parallel arrangement, said holes being spaced on ⅜" centers. The ¼" cable was also attached to an optical spectrophotometric multichannel analyzer (Princeton Instruments) which, in turn, was connected to an IBM-XT computer and associated printer. The flat optical sensor head interfaced with either a PTA powder sample or a PTA pellet employed in determining the b-value.

The scattered light emission spectrum was measured over the range from 372 to 887 nm. A wavelength of 445 nm gave the best correlation to b-value although wavelengths from 440 nm to 465 nm were acceptable. A wavelength of 707 nm was found to be the maximum of one of three carbon-hydrogen stretch overtone bands of PTA. A significant intensity of scattered light, with no significant optical absorption, was found at 675 nm.

EXAMPLE II

The sensor apparatus of Example I was employed in the analysis of 19 samples of PTA, whose b-values ranged from 0.6 to 1.6. Scattered light spectra were obtained on all samples as well as on a highly purified PTA employed as a reference. Data were corrected to constant PTA density and diode values were plotted against the b-value. The observed correlation of data is presented in FIG. 3.

EXAMPLE III

Portions of four samples of powdered kaolin were packaged in transparent polycarbonate plastic boxes having roughly a 2" diameter and ½" thickness. After visually ranking them from dark to light as to color, each package was measured on a Diano Matchscan color measuring spectrophotometer. The determined b-values (yellowness) were in the same order and are presented in Table II.

EXAMPLE IV

Portions of the four kaolin samples employed in Example III were slurried in water to provide a solids content of 30 wt. %. Each slurry was analyzed employing the sensor apparatus of Example I by repeatedly inserting the sensor head into the slurry and measuring the relative transmission of scattered light at three selected wavelengths. A wavelength of 450 nm was employed as charateristic of the impurity components. Wavelengths of 670 and 720 nm were employed as characteristic of the clay products. The averaged values, as well as ratios, are presented in Table II. Reproducibility was found to be about 1%. Good correlations to the respective b-values were observed, even though no marker, intrinsic or extrinsic, was employed.

TABLE I

Optimum Separation of Fiber Optic Elements

| Particle Size Range[a] | Distance Factor[b] |
|---|---|
| 5–20 microns | 1/8 inch |
| 100–500 microns | 3/8 inch |
| 1/8–1/4 inch | 2 inches |

[a] average diameters of particles
[b] spacing of centers of fiber elements

TABLE II

Analysis of Impurity Absorptions
(30 wt. % slurry of kaolin powder in water)

| Sample | b-value | Relative Transmission Value | | | | |
|---|---|---|---|---|---|---|
| | | 450 nm | 670 nm | 720 nm | 450/670 | 450/720 |
| 1 | 9.15 | 1.28 | 1.00 | 2.19 | 1.29 | .585 |
| 2 | 6.08 | 1.53 | 1.14 | 2.46 | 1.32 | .618 |
| 3 | 3.01 | 2.23 | 1.32 | 2.72 | 1.70 | .820 |
| 4 | 5.02 | 1.92 | 1.22 | 2.58 | 1.53 | .744 |

I claim:

1. Optical sensor apparatus for the quantitative determination of the concentration level of at least one impurity component present in a light-scattering product, comprising:
   (a) sampling means, for affording a source of the light-scattering product;
   (b) a reference light source;
   (c) a spectrophotometric analyzer, having a plurality of photodetectors, for the characterization of selected wavelengths of scattered light;
   (d) communication means, having a first end connected to the light source and a second end extending into the sampling means;
   (e) light transmission means, capable of transmitting selected wavelength of scattered light from the sampling means to the plurality of photodetectors within the spectrophotometric analyzer; and
   (f) signal processor means, in communication with the plurality of photodetectors, for processing the characteristics of the selected wavelengths to quantify the concentration level of the respective impurity components in the light-scattering product.

2. Fiber optics sensor apparatus for the quantitative determination of the concentration level of at least one impurity component present in a light-scattering product, comprising:
   (a) sampling means, for affording a source of the light-scattering product;
   (b) a reference light source;
   (c) a spectrophotometric analyzer, having a plurality of photodetectors, for the characterization of selected wavelengths of scattered light;
   (d) a first optical fiber element, having a first end connected to the light source and a second end insertably extending into the sampling means;
   (e) a second optical fiber cable, comprising a plurality of optical fiber elements, having a first end insertably extending into the sampling means, in a spaced relationship to the second end of the first optical fiber element, and having the respective second ends of the plurality of optical fiber elements each separately in communication with one of the plurality of photodetectors within the spectrophotometric analyzer; and
   (f) signal processor means, in communication with the plurality of photodetectors, for processing the characteristics of the selected wavelengths to quantify the concentration level of the respective impurity components in the light-scattering product.

3. The sensor apparatus of claim 2 wherein the source of the light-scattering product is afforded as a process stream.

4. The sensor apparatus of claim 3 wherein the process stream is a flowing process stream.

5. The sensor apparatus of claim 2 wherein the source of the light-scattering product is afforded as a static sample.

6. The sensor apparatus of claim 2 wherein the source of the light-scattering product is afforded as a slurry of a particulate solid dispersed in a liquid composition.

7. The sensor apparatus of claim 2 wherein the light-scattering product is a particulate solid product.

8. The sensor apparatus of claim 2 wherein the light-scattering product is a liquid product.

9. The sensor apparatus of claim 2 wherein the reference light source is a polychromatic light whose spectrum affords useful wavelengths within the range from about 400 nm to about 1000 nm.

10. The sensor apparatus of claim 2 wherein the photodetectors are silicon photodiodes, each including a filter element.

11. The sensor apparatus of claim 2 wherein there are provided optical fiber elements in the second optical fiber cable at least sufficient to transmit scattered light at selected wavelengths characteristic, respectively, of the impurity component concentration levels and the product concentration level.

12. The sensor apparatus of claim 11 wherein there is additionally provided at least one optical fiber element in the second optical fiber cable to transmit scattered light whose wavelength is characteristic of the general intensity of scattered light present within the sampling means.

13. The sensor apparatus of claim 2 additionally including a sensor head member, for receiving optical fiber elements and cables in a selected spaced relationship and maintaining said spaced relationship during insertion into the sampling means.

14. The sensor apparatus of claim 2 wherein the ends of the first optical fiber element and second optical fiber cable inserted into the sampling means are afforded parallel to each other as components of a sensor head member.

15. The sensor apparatus of claim 4 wherein the ends of the first optical fiber element and the second optical fiber cable inserted into the sampling means are afforded parallel to each other as components of a sensor head member and maintained in a plane perpendicular to the plane of flow of the light-scattering product in the process stream.

16. An improved method for the quantitative determination of the concentration level of one or more impurity components present in a light-scattering product, comprising the steps of:
   (a) illuminating a portion of the product with a selected light source;
   (b) transmitting scattered light from the product to a spectrophotometric analyzer, having a photodetector array for the characterization of selected wavelengths of the scattered light;
   (c) observing the intensities of the selected wavelengths characteristic, respectively, of the impurity components and the light-scattering product; and
   (d) correlating the observed intensities of selected wavelengths to a predetermined relationship, whereby a quantitative measure of impurity levels is ascertained.

17. The method of claim 16 wherein the light-scattering product is afforded in a flowing process stream.

18. The method of claim 16 wherein the selected light source is a polychromatic light.

19. The method of claim 16 wherein there is additionally observed a wavelength characteristic of the scattered light.

20. The method of claim 16 wherein illumination of the product is effected by transmission of light from the selected light source through an optical fiber.

21. The method of claim 16 wherein selected wavelengths of scattered light are transmitted from the product through a plurality of optical fiber elements to the spectrophotometric analyzer.

22. The method of claim 16 wherein the light-scattering product is selected from the class consisting of comminuted metal oxides, inorganic salts, clays, minerals, organic derivatives, sugars, polymer chips, solid-liquid slurries, selected liquid-liquid systems and protein materials.

23. The method of claim 22 wherein the organic derivative is an aromatic dibasic acid.

24. The method of claim 23 wherein the selected wavelength characteristic of the aromatic dibasic acid is that of a stretch overtone band.

25. An improved method for the continuous quantitative estimation of the impurity level in terephthalic acid, produced by the oxidation of p-xylene, by non-destructive sampling from a flowing product stream, comprising the steps of:
   (a) illuminating a flowing stream of terephthalic acid with polychromatic light whose spectrum includes useful wavelengths within the range from about 400 nm to about 1,000 nm;
   (b) transmitting scattered light from the flowing stream of terephthalic acid through a fiber optic cable, having a plurality of optical fiber elements, to a spectrophotometric analyzer, having a plurality of photodetectors, each adapted to receive a selected wavelength of scattered light;
   (c) continuously monitoring the intensity signal of light at a wavelength within the range from about 440 to about 465 nm, characteristic of the impurities contained in the terephthalic acid, with a first selected photodetector;
   (d) continuously monitoring the intensity signal of light at a wavelength within the range from about 700 to about 710 nm, characteristic of a carbon-hydrogen stretch overtone band of terephthalic acid, with a second selected photodetector;
   (e) continuously monitoring the intensity signal of light at a wavelength within the range from about 660 to about 680 nm, characteristic of the flowing stream background, with a third selected photodetector; and
   (f) processing the intensity signals from the respective photodetectors, according to a predetermined correlative relationship, whereby the impurity level in terephthalic acid is quantitatively determined.

26. The method of claim 25 wherein the wavelength monitored with the first photodetector is 445 nm.

27. The method of claim 25 wherein the wavelength monitored with the second photodetector is 703 nm.

28. The method of claim 25 wherein the wavelength monitored by the third photodetector is 675 nm.

29. An improved method for the continuous quantitative estimation of the impurity level in a processed clay, comprising the steps of:
   (a) preparing a homogeneous aqueous slurry containing from about 15 to about 50 wt. % particulate processed clay;
   (b) illuminating the aqueous clay slurry with polychromatic light whose spectrum includes useful wavelengths within the range from about 400 nm to about 1,200 nm;
   (c) transmitting scattered light from the aqueous clay slurry through a fiber optic cable, having a plurality of optical fiber elements, to a spectrophotometric analyzer, having a plurality of photodetectors, each adapted to receive a selected wavelength of scattered light;
   (d) continuously monitoring the intensity signal of light at a wavelength within the range from about 440 to about 460 nm, selected as characteristic of the impurities contained in the processed clay, with a first selected photodetector;
   (e) continuously monitoring the intensity signal of light at a wavelength within the range from about 660 nm to about 730 nm, selected as characteristic of the processed clay, with a second selected photodetector; and
   (f) processing the intensity signals from the respective photodetectors, according to a predetermined correlative relationship, whereby the impurity level the processed clay is quantitatively determined.

30. The method of claim 29 wherein the homogeneous aqueous slurry contains from about 25 to about 35 wt. % particulate processed clay.

31. The method of claim 29 wherein the processed clay is a kaolin and the wavelength selected as characteristic of the impurities is 450 nm.

32. The method of claim 31 wherein the wavelength selected as characteristic of the kaolin is 670 nm.

33. The method of claim 31 wherein the wavelength selected as characteristic of the kaolin is 720 nm.

34. The method of claim 29 wherein a minor amount of an external marker substance is added to the processed clay, whereby continuous monitoring of the intensity signal of light at a selected wavelength, characteristic of said external marker substance, provides a reference value characteristic of the slurry background.

35. The method of claim 32 wherein the external marker substance is selected from the class consisting of dyes, metallic ions, and mixtures thereof.

* * * * *

UNITED STATES PATENT OFFICE
CERTIFICATE OF CORRECTION

Patent No. 4,755,048      Dated July 5, 1988

Inventor(s) R. Gilbert Kaufman

It is certified that error appears in the above-identified patent and that said Letters Patent is hereby corrected as shown below:

Column 10, lines 37 & 38, "level the" should read --level of the--.

Signed and Sealed this

Eighteenth Day of July, 1989

Attest:

DONALD J. QUIGG

Attesting Officer        Commissioner of Patents and Trademarks